US00PP19309P2

(12) United States Plant Patent
Gitzels

(10) Patent No.: US PP19,309 P2
(45) Date of Patent: Oct. 7, 2008

(54) *DAHLIA* PLANT NAMED 'BALDELMIM'

(50) Latin Name: *Dahlia variabilis*
Varietal Denomination: Baldelmim

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/823,203

(22) Filed: Jun. 27, 2007

(51) Int. Cl.
*A01H 5/00* (2006.01)

(52) U.S. Cl. ..... Plt./321

(58) Field of Classification Search ..... Plt./321
See application file for complete search history.

(56) References Cited

U.S. PATENT DOCUMENTS

PP16,518 P2 * 5/2006 Gitzels ..... Plt./321

* cited by examiner

*Primary Examiner*—Wendy C. Haas
(74) *Attorney, Agent, or Firm*—Audrey Charles

(57) ABSTRACT

A new and distinct cultivar of *Dahlia* plant named 'Baldelmim', characterized by its double type white-colored flowers, medium green-colored foliage, and moderately vigorous, upright-mounded growth habit.

1 Drawing Sheet

Latin name of genus and species of plant claimed: *Dahlia variabilis*.
Variety denomination: 'Baldelmim'.

BACKGROUND OF THE INVENTION

The present invention relates to a new and distinct cultivar of *Dahlia* plant botanically known as *Dahlia variabilis* and hereinafter referred to by the cultivar name 'Baldelmim'.

The new cultivar originated in a controlled breeding program in Rijsenhout, the Netherlands during July 1999. The objective of the breeding program was the development of *Dahlia* cultivars that are freely flowering with large flowers and a moderately vigorous growth habit.

The new *Dahlia* cultivar is the result of open-pollination. The female (seed) parent of the new cultivar is the proprietary *Dahlia variabilis* breeding selection designated 3236, not patented, characterized by its double type white-colored flowers, medium green-colored foliage, and semi-upright growth habit. The male (pollen) parent of the new cultivar is unknown. The new cultivar was discovered and selected as a single flowering plant within the progeny of the above stated open-pollination during September 2000 in a controlled environment at Rijsenhout, the Netherlands.

Asexual reproduction of the new cultivar by terminal stem cuttings since September 2000 at Rijsenhout, the Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baldelmim' as a new and distinct cultivar of *Dahlia* plant:

1. Double type, white-colored flowers;
2. Medium green-colored foliage; and
3. Moderately vigorous, upright-mounded growth habit.

Plants of the new cultivar differ from plants of the female parent primarily in flower color and flower size. Plants of the new cultivar have milky white-colored flowers whereas plants of the female parent have plain white-colored flowers.

Of the many commercially available *Dahlia* cultivars, the most similar in comparison to the new cultivar is Delicious™ Marshmallow 'Baldelmalo', U.S. Plant Pat. No. 16,518. However, in side by side comparisons, plants of the new cultivar differ from plants of 'Baldelmalo' in the following characteristics:

1. Plants of the new cultivar are shorter than plants of 'Baldelmalo';
2. Plants of the new cultivar have fewer ray florets than plants of 'Baldelmalo'; and
3. Plants of the new cultivar have longer peduncles than plants of 'Baldelmalo'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldelmim'. The plants were grown in 4.5 inch pots for 9 weeks in a greenhouse at West Chicago, Ill.

DETAILED BOTANICAL DESCRIPTION

Figure 1:
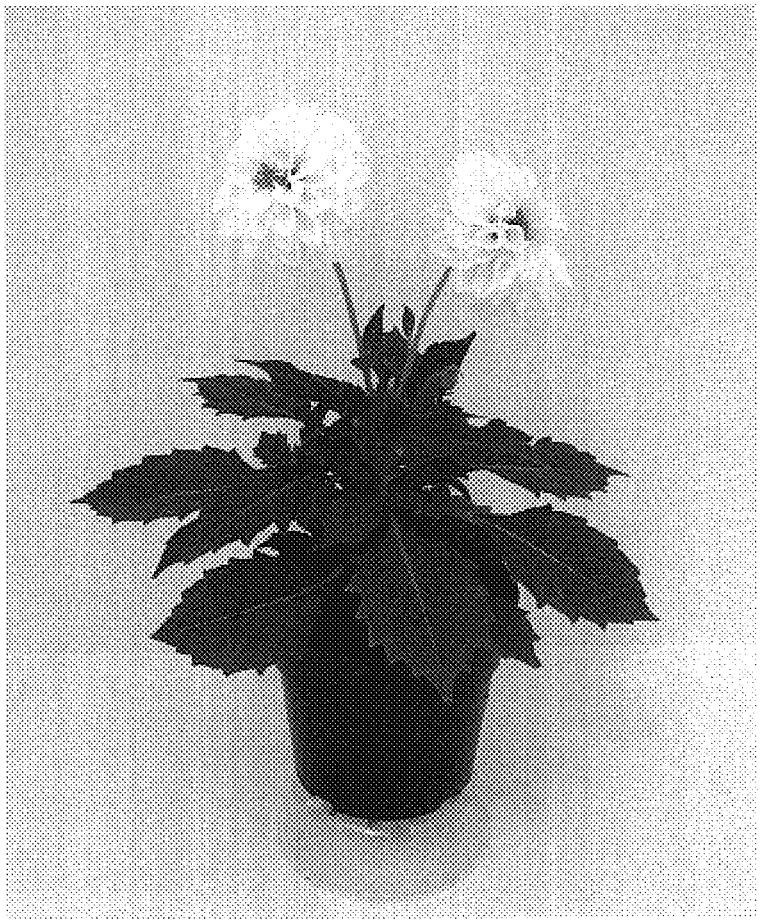
FIG. 1 illustrates a side view of the overall growth and flowering habit of 'Baldelmim'.
Figure 2:
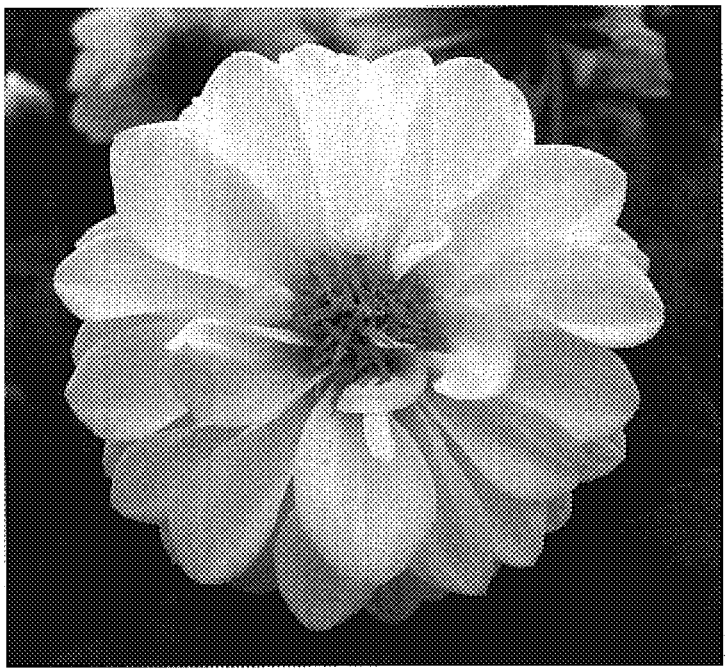
FIG. 2 illustrates a close-up view of an individual inflorescence of 'Baldelmim' with ray florets and disc florets fully opened.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 4, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Dahlia variabilis* cultivar Baldelmim.

Parentage:

*Female parent.*—Proprietary *Dahlia variabilis* breeding selection designated 3236, not patented.

*Male parent.*—Unknown.

Propagation:

*Type cutting.*—Terminal stem.

*Time to initiate roots.*—Approximately 7 to 10 days.

*Time to produce a rooted cutting.*—Approximately 28 to 32 days.

*Root description.*—Fine, fibrous.

*Rooting habit.*—Freely branching.

*Tuber formation.*—Will form under short day conditions of at least 13 to 14 hours of darkness.

Plant description:

*Commercial crop time.*—Approximately 8 to 10 weeks from a rooted cutting to finish in a 15 cm pot.

*Growth habit.*—Moderately vigorous, mounded.

*General appearance.*—Upright.

*Size.*—Height from soil level to top of plant plane: Approximately 23.5 cm. Height from soil level to top of foliage: Approximately 12.6 cm. Width: Approximately 22.9 cm.

*Branch.*—Quantity of lateral branches per plant: Approximately 4. Strength: Strong. Length of lateral branch: Approximately 7.9 cm. Diameter of lateral branch at central internode: Approximately 3.1 mm. Texture: Glabrous. Color: 144A. Length of central internode of lateral branch: Approximately 1.1 cm.

*Foliage.*—Quantity of leaves per lateral branch: Approximately 10. Type: Simple and compound. Quantity of leaflets per compound leaf: Approximately 3. Fragrance: None. Arrangement: Opposite. Aspect: Petiole is acute angle to stem; blade is perpendicular to stem. Shape of leaf and leaflet: Elliptic. Margin of leaf and leaflet: Widely serrate. Apex of leaf and leaflet: Acuminate. Base of leaf and leaflet: Attenuate. Venation pattern: Pinnate.

*Simple leaf.*—Length: Approximately 8.2 cm. Width: Approximately 5.1 cm. Texture of upper and lower surfaces: Sparsely pubescent on venation. Color of upper surface: 137A with venation of 146B. Color of lower surface: 191B with venation of 146B. Length of petiole: Approximately 2.9 cm. Diameter of petiole: Approximately 3.0 mm. Texture of upper and lower surfaces of petiole: Glabrous. Color of upper and lower surfaces of petiole: 145A.

*Mature trifoliate leaf.*—Length of mature trifoliate leaf: Approximately 7.9 cm. Width of mature trifoliate leaf: Approximately 8.8 cm. Length of terminal leaflet: Approximately 7.5 cm. Width of terminal leaflet: Approximately 3.8 cm. Length of lateral leaflet: Approximately 4.8 cm. Width of lateral leaflet: Approximately 2.8 cm. Texture of upper surface: Sparsely pubescent on venation. Texture of lower surface: Sparsely pubescent on venation. Color of upper surface: 137A with venation of 146B. Color of lower surface: 191B with venation of 146B. Length of petiole of mature trifoliate leaf: Approximately 3.3 cm. Diameter of petiole of mature trifoliate leaf: Approximately 3.0 mm. Texture of upper and lower surfaces of petiole of mature trifoliate leaf: Glabrous. Color of upper and lower surfaces of petiole of mature trifoliate leaf: 145A. Length of rachis: Approximately 4.2 mm. Diameter of rachis: Approximately 3.0 mm. Texture of upper surface of rachis: Sparsely pubescent. Texture of lower surface of rachis: Glabrous. Color of upper and lower surfaces of rachis: 145A.

Flowering description:

*Flowering habit.*—'Baldelmim' is freely flowering under outdoor growing conditions with substantially continuous blooming from spring through autumn and year-round in greenhouse environment.

*Lastingness of individual inflorescence on the plant.*—Approximately 6 days.

Inflorescence description:

*Appearance.*—Type: Composite, daisy-eyed double, persistent. Aspect: Facing outward. Flower arrangement: Terminal, arising from leaf axils on strong peduncles positioned over the foliage. Disc and ray florets arranged acropetally on a capitulum.

*Quantity per plant.*—Approximately 2.

*Fragrance.*—None.

*Shape/size.*—Hemispherical when ray florets are fully open. Inflorescence diameter: Approximately 7.1 cm. Inflorescence depth: Approximately 3.6 cm. Disc diameter: Approximately 1.4 cm. Receptacle diameter at base: Approximately 9.0 mm. Receptacle depth: Approximately 3.0 mm. Receptacle color: 145B.

*Peduncle.*—Strength: Strong. Aspect: Erect. Length: Approximately 9.1 cm. Diameter: Approximately 3.0 mm. Texture: Glabrous. Color: 144B.

*Bud.*—Rate of bud opening: Approximately 8 days. Quantity per plant: Approximately 1. Shape: Oblate. Depth at first color: Approximately 1.2 cm. Diameter at first color: Approximately 1.5 cm. Texture at first color: Glabrous. Color: Outer surface of phyllaries is 154B with base of 144B and petal of 158D.

*Ray florets.*—Quantity per inflorescence: Approximately 37. Arrangement: Imbricate, in multiple whorls. Aspect: Cupped. Shape: Ovate. Margin: Entire. Apex: Acute. Base: Fused into a short corolla tube. Appearance: Dull. Length: Approximately 3.5 cm. Width: Approximately 1.9 cm. Texture of upper and lower surfaces: Glabrous. Color of upper surface when first and fully open: 155A with base of 154C. Color of lower surface when first and fully open: 155A with base of 154D.

*Disc florets.*—Quantity per inflorescence: Approximately 39. Arrangement: Massed in center of inflorescence. Aspect: Erect. Shape: Tubular. Margin: Entire. Apex: 5 acute downward turning tips. Base: Fused. Length: Approximately 1.2 cm. Diameter at apex: Approximately 3.0 mm. Diameter at base: Approximately 1.0 mm. Texture: Glabrous. Color when fully open: 1B, translucent.

*Outer phyllaries.*—Quantity: Approximately 5 to 6. Aspect: Flat. Shape: Rhombic. Margin: Entire. Apex: Acute. Base: Truncate. Length: Approximately 1.1 cm. Width: Approximately 4.0 mm. Texture of upper and lower surfaces: Glabrous. Color of upper and lower surfaces: 137A.

*Inner phyllaries.*—Quantity: Approximately 1 per floret. Shape: Linear, imbricate. Margin: Entire. Apex: Broadly acute. Base: Truncate. Length of outermost: Approximately 1.5 cm. Width of outermost: Approximately 5.4 mm. Length of innermost: Approximately 9.0 mm. Width of innermost: Approximately 2.0 mm. Texture of upper and lower surfaces of all inner phyllaries: Glabrous. Color of upper and lower surfaces: 154C, translucent with a base of 143A for outermost.

*Reproductive organs.*—Androecium: On disc florets. Stamen quantity: 5 per floret. Anther shape: Linear. Anther length: Approximately 3.0 mm. Anther color: 14B, translucent. Pollen amount: Abundant. Pollen color: 14A. Gynoecium: On disc and ray florets. Pistil length: Approximately 1.2 cm. Stigma shape: 2 branches. Stigma length: Approximately 3.0 mm. Stigma color: 13A. Style length: Approximately 8.4 mm. Style color: 145C. Ovary diameter: Approximately 1.0 mm. Ovary color: 145D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelmim', substantially as herein shown and described.

* * * * *